United States Patent [19]

Kapmeyer et al.

[11] Patent Number: 5,232,859
[45] Date of Patent: Aug. 3, 1993

[54] METHOD FOR THE NEPHELOMETRIC OR TURBIDIMETRIC DETERMINATION OF PROTEINS IN THE PRESENCE OF A SURFACTANT AND AN AGENT THEREFOR

[75] Inventors: Wolfgang Kapmeyer; Rudolf Schmidtberger, both of Marburg, Fed. Rep. of Germany

[73] Assignee: Behringwerke Aktiengesellschaft, Marburg/Lahn, Fed. Rep. of Germany

[21] Appl. No.: 196,529

[22] Filed: May 20, 1988

[30] Foreign Application Priority Data

May 23, 1987 [DE] Fed. Rep. of Germany ....... 3717402

[51] Int. Cl.$^5$ ................ G01N 33/543; G01N 33/547
[52] U.S. Cl. .................... 436/518; 436/533; 436/826
[58] Field of Search ............ 436/518, 826, 533, 825; 435/962

[56] References Cited

U.S. PATENT DOCUMENTS

| | | | |
|---|---|---|---|
| 4,148,869 | 4/1979 | Deaton | 436/513 |
| 4,282,001 | 8/1981 | Klose et al. | 436/174 |
| 4,311,788 | 1/1982 | Heuck | 435/7.1 |
| 4,448,908 | 5/1984 | Pauly et al. | |
| 4,639,425 | 1/1987 | Baier | 436/533 |
| 4,810,630 | 3/1989 | Craig et al. | 435/962 |
| 4,921,915 | 5/1990 | Dengler et al. | 436/531 |

FOREIGN PATENT DOCUMENTS 0080614  4/1987  European Pat. Off. .
187862  11/1983  Japan .

OTHER PUBLICATIONS

R. E. Ritchie, in N. R. Rose et al (eds.), *Methods in Immunodiagnosis*, John Wiley & Sons, Inc., 1980, pp. 91–100.
J. of Immunoassay, 4(3), 209–327 (1983).

*Primary Examiner*—David Saunders
*Attorney, Agent, or Firm*—Finnegan, Henderson, Farabow, Garrett & Dunner

[57] ABSTRACT

A method for the determination of a partner in an immunochemical reaction, in which one of the partners, which is dissolved in an aqueous fluid, is allowed to react with the other partner, which is covalently bonded to a solid phase, which comprises allowing the reaction to take place in the presence of 0.1 to 3 g/100 g of the aqueous fluid of a surfactant of the formula I $$CH_3-(CH_2)_m-R-(CH_2-CH_2-O)_n-H \qquad I$$

in which R is O, NH or $CH=CH-(CH_2)_p-O$ with m being 3–26, n being 7–40 and p being 5–15, and an agent suitable for this purpose, are described.

7 Claims, No Drawings

METHOD FOR THE NEPHELOMETRIC OR TURBIDIMETRIC DETERMINATION OF PROTEINS IN THE PRESENCE OF A SURFACTANT AND AN AGENT THEREFOR

The invention relates to a method for the quantitative determination of proteins in body fluids with the aid of a solid-phase immunological reaction between an antigen and an antibody, one of which is bound to the solid-phase, in the presence of a surfactant, and to the use of a surfactant for this purpose.

Numerous nephelometric and turbidimetric methods are known for the quantitative determination of immunoglobulins and other serum proteins. The lower detection limit of these methods is about 5 μg/ml. This sensitivitiy is inadequate for many diagnostic objectives.

It is known to increase the sensitivity of immunological determination methods by using indicator or carrier particles which are loaded with one of the immunochemical reactants in the relevant method. It is possible to use as carrier material, for example, red blood cells, cells from a cell culture or particulate polymers, especially latex particles with a diameter of 0.02 to 5 μm.

A "particle-enhanced" nephelometric or turbidimetric assay of this type can reliably determine proteins down to concentrations of about 50 ng/ml.

An antibody bound to a solid phase is used for the determination of an antigen, and an antigen bound to a solid phase is used for the determination of an antibody. In both cases, the polymer particles agglutinate due to the immunological reaction. This results in an increase in the size of the agglutinates, and there is an increase in the scattered light signal or the turbidity of the reaction mixture.

In a particle-enhanced nephelometric or turbidimetric assay or an enzyme immunoassay, immunological reactions take place on solid phases. Non-specific adsorption of proteins from the sample is a property of these solid phases. When analytes from serum or other body fluids are measured it is possible for albumin, globulins or lipoproteins, for example, to result in covering of the solid phase. This may lead to the immunologically reactive components on the solid phase being concealed.

The consequence of this in determinations of trace proteins in body fluids is that the results are incorrect, too low and variable. However, measurements which are incorrect and too high are also obtained. Both cases, results which are incorrect and too low and incorrect and too high, occur in measurements with particle-enhanced reagents of the state of the art, and thus prevent reliable and reproducible measurement.

EP-A 0,133,272 (U.S. Pat. No. 4,448,908) discloses a method in which a detergent is added, preferably in a concentration of up to 0.01%, to the incubation medium of an immunological reaction between a soluble partner and a partner adsorbed on a solid phase.

It has been found, surprisingly, that interference, deriving from the "serum matrix", in solid-phase immunological reactions such as particle-enhanced nephelometric or turbidimetric assays in which the partner in the immunological reaction which is bound to the solid phase is covalently bonded can be avoided by carrying out the measurement in the presence of a compound of the formula I $$CH_3-(CH_2)_m-R-(CH_2-CH_2-O)_n-H \quad I$$

in which
$R=O$, NH or $CH=CH-(CH_2)_p-O$ with $m=3-26$, $n=7-40$ and
$p=5-15$.

Hence the invention relates to a method for the determination of a partner in an immunochemical reaction, in which one of the partners, which is dissolved in an aqueous fluid, is allowed to react with the other partner, which is covalently bonded to a solid phase, which comprises allowing the reaction to take place in the presence of a compound of the formula I with the definitions stated.

A compound of the formula I with $R=$or $CH=CH-(CH_2)_p13$ O and $m=3-26$, $n=7-40$ and $p=5-15$ is preferred, and with $m=15-17$, $n=25$ and $p=6-8$ is particularly preferred, and with $m=6-8$, $n=25$ and $p=6-8$ is very particularly preferred.

Also particularly preferred is a mixture of compounds of the formula I which contains 20–35% of palmityl alcohol etherified with polyethylene glycol with a degree of polymerization of $P=25$, 15–30% of stearyl alcohol etherified with polyethylene glycol ($P=25$) and 30–60% of oleyl alcohol etherified with polyethylene glycol ($P=25$) and which is marketed under the name ®GENAPOL T 250 by Hoechst AG, Frankfurt, FRG.

Another particularly preferred mixture of compounds of the formula I is one which is marketed under the name ®LUBROL PX by Sigma.

The compound or compounds of the formula I are added in an amount such that a concentration of more than 0.01 and up to 3 g/100 g, preferably 0.1 to 1 g/100 g, of fluid is reached.

The reaction mixture can also contain an amino acid, preferably glycine, preferably in a concentration of 0.05–0.2 mol/l, a neutral salt, preferably sodium chloride, in a concentration of 0.05–0.5 mol/l polyethylene glycol, preferably in a concentration of 4 g/100 g and/or eicosaoxyethylene sorbitan laurate (®Tween 20), preferably in a concentration of 0.2–1 g/100 g.

The compound of the formula I is preferably added to the 0.1M glycine buffer, pH 8.0. Incubation with the serum which is to be assayed is preferably carried out at room temperature for about 30 minutes, and measurement is preferably in a nephelometer.

The use of covalently bonded reactants represents an advantage because of the possible non-specific detachment of adsorbed reactants. The use of a detergent concentration of up to 3 g/100 g means a very much greater efficacy of the detergent with regard to interfering effects, and it is possible in this way to carry out nephelometric or turbidimetric particle-enhanced assays from which interfering factors have been eliminated.

Particularly suitable as the solid phase are latex particles in the form of a dispersion.

It is possible to use for the covalent bonding of an antibody or antigen to such particles, for example, latices which carry carboxyl groups which can be converted into activated esters or can be activated with carbodiimides and reacted with the antibody or the antigen. However, it is also possible to use latices carrying epoxy, aldehyde or aromatic amino groups, it being possible to bring about the covalent bonding in the case of aldehyde groups by reductive amination, and in the case of aromatic amino groups by diazotization.

An antibody or antigen bound to a solid phase is preferably prepared by reacting an antibody or antigen with a latex carrying acetal groups, as is described in EP-A 0,080,614.

The antibodies preferably bonded to the solid phase are those against alpha-fetoprotein (AFP), ferritin, carcinoembryonic antigen (CEA), myoglobin, beta-2 microglobulin or immunoglobulin E.

If an AFP assay obtained in this way is carried out without a compound of the formula I, then the results obtained for 20 different sera, to all of which have been added 200 ng/ml AFP, vary widely (Table 1). A mean of only 90.8% of the AFP used is found. The coefficient of variation is very high at 17.5%.

In contrast, if the AFP assay is carried out with the addition of 1 g/100 ml ®GENAPOL, then the result found for 20 different sera, to which 200 ng/ml AFP have been added, is always correct, irrespective of the serum (Table 1), that is to say the amount of AFP introduced is found again.

TABLE 1

Measurements in the nephelometric assay (concentration of AFP added: 200 ng/ml)

| Serum No. | AFP concentration found (ng/ml) | |
|---|---|---|
| | State of the art | According to the invention |
| 1 | 153 | 188 |
| 2 | 181 | 198 |
| 3 | 169 | 203 |
| 4 | 136 | 194 |
| 5 | 169 | 189 |
| 6 | 155 | 197 |
| 7 | 248 | 216 |
| 8 | 168 | 196 |
| 9 | 207 | 212 |
| 10 | 200 | 192 |
| 11 | 159 | 186 |
| 12 | 190 | 199 |
| 13 | 179 | 200 |
| 14 | 140 | 188 |
| 15 | 174 | 188 |
| 16 | 161 | 196 |
| 17 | 256 | 214 |
| 18 | 173 | 188 |
| 19 | 212 | 202 |
| 20 | 201 | 185 |
| Mean of the measurements: | 181.6 | 196.6 |
| Coefficient of variation: | 17.5% | 4.7% |
| Recovery: | 90.8% | 98% |

A mean recovery of 98% of the AFT introduced is found. The coefficient of variation is very low at 4.7%. The recovery of the AFP concentrations is correct.

The disadvantages of an AFP assay without the addition, according to the invention, of a surfactant are also evident from the fact that state of the art nephelometric and turbidimetric measurements give results which do not agree well with the AFP concentrations present. A state of the art nephelometric measurement of AFP using latices as in Example 3 is unsatisfactory, in comparison with the concentrations of AFP introduced, having a correlation coefficient of 0.910 and a slope of 0.83 in the regression analysis.

In contrast, if the same number of nephelometric measurements of AFP are carried out with the addition, according to the invention, of a surfactant, namely of ®GENAPOL (1 g/100 g in the assay buffer), then the recovery of the amounts of AFP introduced into the patients' sera is satisfactory. The slope in the regression analysis is 0.99, and the correlation coefficient is 0.998.

Furthermore, a state of the art nephelometric determination of ferritin has been carried out, and the results have been compared with those from an enzyme immunoassay (from Abbott). The agreement between the two methods is unsatisfactory. Regression analysis yields a slope of 0.764 and a correlation coefficient of 0.726. The mean deviation between the two methods for a collection of sera is 46%.

In contrast, if a ferritin assay of this type is carried out with 1 g/100 g ®Genapol in the assay buffer, then the agreement with the results of the enzyme immunoassay is found to be better. Regression analysis shows a slope of 0.945 and a correlation coefficient of 0.857. The mean deviation between the two methods for a collection of sera is 20%.

The examples which follow illustrate the invention.

EXAMPLE 1

1. Preparation of Seed Polymer 310 ml of nitrogen-saturated double-distilled water were placed in a cylindrical glass vessel equipped with gas inlet and gas outlet tubes and a magnetic stirring bar. 500 mg of sodium stearate were added to this and dissolved by stirring. 1.5 ml of 25% strength ammonia were subsequently added to this. The pH was checked and was found to be 11.09. Oxygen was removed from the polymerization vessel by repeated evacuation and filling with nitrogen. While stirring continuously, the detergent solution was heated to +70° C. with the aid of a water bath. A pressure-equalizing dropping funnel was then used to introduce 90 ml of freshly distilled styrene into the polymerization vessel under nitrogen. The mixture was stirred at +70° C. for a further 15 minutes to emulsify the styrene. The temperature was then raised to +90° C., and stirring was continued for one hour. Thereafter 67.5 mg of potassium peroxodisulfate dissolved in 50 ml of nitrogen-saturated distilled water were added thereto. The mixture was left to stir at +90° C. for 130 minutes. The polystyrene was passed through a fluted filter. In some instances this results in a few ml of styrene remaining on the filter. This styrene could not, because present in somewhat of an excess, be completely dissolved in the polystyrene.

The filtered polystyrene was dialyzed against 10 liters of 0.01% strength ammonium bicarbonate solution (with 0.01% NH$_4$HCO$_3$; 0.01% by weight NaN$_3$; adjusted to pH 10.0 with 10.5 ml of 25% by weight ammonia in 10) for 50 hours. After dialysis, 410 ml of polymer with a dry weight of 17.9 g/dl were obtained. About 85% of the monomer used has thus been polymerized. In contrast, it was possible to reduce the proportion of completely polymerized styrene, with a simultaneous increase in the monomer dissolved in the polystyrene, by reducing the polymerization time by 5 to 10 minutes.

2. Synthesis of N-(2,3-dihydroxypropyl)methacrylamide 4.65 g of 3-amino-1,2-propanediol (0.05 mol) were dissolved in 30 ml of dimethylformamide (anhydrous). This solution and 13.8 g of K$_2$CO$_3$ were placed in a 100 ml three-necked flask with dropping funnel and gas inlet and gas outlet tubes. The mixture was cooled to 0° C. in an ice bath. While stirring gently and slowly bubbling nitrogen through, 6.18 ml of methacryloyl chloride (0.06 mol) dissolved in 30 ml of dimethylformamide were added dropwise over the course of 30 minutes. The mixture was stirred, while cooling in ice, for a further hour and then allowed to warm to room temperature and was stirred for a further 30 minutes. The reaction mixture was filtered through a fluted filter, and the residue was discarded. The filtrate was concentrated to a viscous oil in a rotary evaporator. This oil was dissolved in 30 ml of methanol, a second filtration was carried out, and the filtrate was again concentrated in a rotary evaporator. The residues of the solvent were removed under high vacuum. The yield was 8.52 g.

3. Polymerization of N-(2,3-Dihydroxypropyl)Methacrylamide (NDPM) On Seed Polymer 21.75 ml of a polystyrene latex dispersion prepared as in Example 1, with a solids content of 18.39% by weight, and 57.25 ml of distilled water and 50 mg of sodium dodecyl sulfate were placed in a cylindrical glass vessel equipped with gas inlet and gas outlet tubes and a magnetic stirring bar and stirred to dissolve. Oxygen was removed from the polymerization vessel by repeated evacuation and filling with nitrogen. The latex/detergent mixture was heated to +70° C. in a water bath, stirring continuously. 1 ml of a potassium peroxodisulfate solution (16 mg/ml in distilled water) was added thereto.

A monomer mixture was prepared from 0.2 ml of styrene, 0.4 ml of methacrylamidoacetaldehyde di-n-pentyl acetal, 0.010 ml of methacrylic acid and 0.4 ml of the N-(2,3-dihydroxypropyl)methacrylamide (NDPM) obtained in 2., together with 0.2 ml of dimethylformamide to improve the solubility of these monomers.

The mixture of monomers was slowly added dropwise, over the course of 60 minutes, to the vigorously stirred polystyrene latex suspension. The temperature of the polymerization mixture was maintained at +70° C. The dropwise addition of the monomer mixture was followed by stirring at the said temperature for a further 5 hours. This completed the polymerization, and the dispersion was cooled to room temperature and filtered using a fluted filter. 73 ml of a latex suspension were obtained. This was then dialyzed against an NaHCO$_3$ buffer solution (0.25 g/l, pH 8-8.2) for 17 hours. 74 ml of a latex dispersion with a solids content of 4.7% by weight were obtained.

4. Polymerization of 2-Hydroxypropyl Methacrylate HPM On Seed Polymer

The polymerization was carried out in a way similar to that described in 3. A mixture of 22.4 ml of polystyrene latex, prepared as in 1. and with a solids content of 17.9% by weight, and 56.7 ml of distilled water and 50 mg of sodium dodecyl sulfate was prepared. This was placed in the polymerization vessel, and the oxygen was removed. 1 ml of a potassium peroxodisulfate solution (16 mg/ml in distilled water) was then added thereto, and the mixture was heated to +70° C. A mixture of 0.4 ml of styrene, 0.4 ml of methacrylamidoacetaldehyde di-n-pentyl acetal, 0.025 ml of methacrylic acid and 0.2 ml of 2-hydroxypropyl methacrylate (HPM) was prepared. The monomer mixture was slowly added dropwise to the vigorously stirred polystyrene latex suspension over the course of 60 minutes at +70° C. Stirring was then continued at the same temperature for a further 5 hours.

Cooling to room temperature and filtration through a fluted filter resulted in 73 ml of the polymer. It was then dialyzed against NaHCO$_3$ buffer (0.25 g/l, pH 8-8.2) for about 20 hours. 87 ml of a latex dispersion with a solids content of 5.1% were obtained.

5. Bonding of Anti-AFP Antibodies to a Polymer

Anti-AFP antibodies were bonded to a polymer prepared as in 3. using N-(2,3-dihydroxypropyl)methacrylamide.

The polymer used in each case was diluted with distilled water to a solids content of 4% by weight. An antiserum obtained by immunization of rabbits with purified AFP was purified by affinity chromatography by known methods. It was then concentrated until a protein content of 10 mg/ml was reached.

3.4 ml of the abovementioned polymer were mixed with 0.34 ml of the anti-AFP antibody solution. Then 0.17 ml of a 20% strength aqueous solution of eicosaoxyethylene sorbitan laurate (®Tween 20) was added thereto, and mixing was again carried out. We then added 0.05 ml of 1N HCl to this so that a pH of about 2 was reached. After an incubation time of 30 minutes at room temperature, we added 0.85 ml of saturated aqueous sodium hydrogen phosphate solution (pH 6.5) and 0.85 ml of aqueous sodium cyanoborohydride solution (25 mg/ml) thereto, and mixed thoroughly. This was followed by incubation at room temperature for one hour.

This coating mixture was then centrifuged at about 50,000 × g for 30 minutes (Beckman centrifuge, 20,000 r.p.m.).

The supernatnat was discarded. The residue was resuspended in 5 ml of a glycine/NaCl buffer (0.1 mol/l glycine, 0.17 mol/l NaCl, 0.5% eicosaoxyethylene sorbitan laurate (®Tween 20), pH 8.2). This was followed by treatment with ultrasound (Branson B 15 Sonyfier) for 2 seconds. The reagent which had been redispersed in this way was diluted in the ratio 1:60 by volume with the abovementioned glycine/NaCl buffer.

6. Measurement of AFP Concentrations In Serum Samples

The reagent, prepared as in 5. by bonding of anti-AFP antibodies to latex preparations according to the invention, for the determination of AFP was used for measuring AFP in sera to which known amounts have been added. The standard used was the alpha-fetoprotein standard serum (human) for immunoprecipitation with an AFP concentration of 322,000 ng/ml (from Behringwerke AG). The standard was diluted to 1,000 ng/ml in a pooled AFP-free serum. This dilution was further diluted stepwise, doubling the volume each time, in the pooled AFP-free serum. This resulted in a standard series with decreasing AFP concentrations. The standard sera, as well as the patients' sera to be determined, were diluted 1:5 in a glycine/sodium chloride buffer (0.1M glycine, 0.17M Nacl, pH 8.2). For the measurement, 20 μl of patient's serum dilution or standard serum dilution were pipetted with 150 μl of a reaction buffer (0.1M glycine, 0.17M NaCl, 4% polyethylene glycol (PEG) 6,000, 0.5% ®Tween 20, pH 8.2) into BLN cuvettes (from Behringwerke AG). After a reaction time of 12 min the cuvettes were then measured in a laser nephelometer (from Behringwerke AG).

The reference plot for the measurement of the standard serum was drawn on semilogarithmic paper and used to evaluate the measurements for the patients' sera.

EXAMPLE 2

1. Bonding of Anti-Ferritin Antibodies to a Polymer

A polymer prepared using 2-hydroxypropyl methacrylate as in Example 1.4. was diluted with distilled water to a solids content of 4% by weight. An antiserum obtained by immunization of sheep with purified liver ferritin was purified by affinity chromatography by a known method It was then concentrated until a protein content of 12 mg/ml was reached.

0.5 ml of the abovementioned polymer was mixed with 0.050 ml of the anti-liver ferritin antibody solution (diluted to 5 mg/ml with isotonic sodium chloride solution). Then 0.025 ml of a 20% strength aqueous solution of eicosaoxyethylene sorbitan laurate (®Tween 20) was added thereto, and mixing was again carried out. We added 0.010 ml of 1N HCl thereto so that a pH of about 2 was reached. After an incubation time of 30 minutes at room temperature, we added 0.125 ml of saturated aqueous sodium hydrogen phosphate solution (pH 6.5) and 0.125 ml of aqueous sodium cyanoborohydride solution (25 mg/ml) thereto and mixed thoroughly. This was followed by incubation at room temperature for one hour. This coating mixture was then centrifuged at about 50,000 × g for 30 minutes (Beckman centrifuge, 20,000 r.p.m.). The supernatant was discarded. The residue was resuspended in 0.75 ml of a glycine/NaCl buffer (0.1M glycine, 0.17M NaCl, 0.5% eicosaoxyethylene sorbitan laurate (®Tween 20) pH 8.2).

This was followed by treatment with ultrasound (Branson B 15 Sonyfier) for 2 seconds. The reagent redispersed in this way was initially diluted in the ratio 1:30 by volume with 0.05M imidazole+6% sucrose+0.1% human albumin and further diluted 1:2 with distilled water.

2. Measurement of Ferritin Concentrations In Serum Samples

The reagent, prepared by binding of anti-liver ferritin antibodies to the latex preparation, for the determination of ferritin was used for measuring ferritin in patients' sera.

The standard used was a ferritin standard from the Enzygnost assay (from Behringwerke AG). This ferritin standard contained 20,000 ng/ml. The standard was diluted in a pooled ferritin-free serum initially to 10,000 ng/ml and then further to 1,250 ng/ml. The latter was used to produce geometrical serial dilutions (5 dilution steps with a factor of 2). The standard sera, as well as the patients' sera to be determined, were diluted 1:5 in a glycine/sodium chloride buffer (0.1M glycine, 0.17M Nacl, pH 8.2). For the measurement, 20 μl of patient's serum dilution or standard serum dilution were mixed with 150 μl of a reaction buffer (0.17M NaCl, 0.1 M glycine, 0.11% Na azide+0.2% BSA+0.02% benzamidinium chloride, 4% PEG 6,000, 0.5% ®Tween 20, pH 8.2) with the addition of 1% ®GENAPOL T 250 (from Hoechst AG) in BLN cuvettes (from Behringwerke AG), and the mixture was incubated at room temperature for 30 minutes. The cuvettes were then measured in a laser nephelometer (from Behringwerke AG).

The reference plot for the measurement of the standard sera was drawn on semilogarithmic paper and used to evaluate the measurements for the patients' sera.

We claim:

1. A method for the nephelometric or turbidimetric determination in an aqueous fluid of an antibody or antigen comprising the steps of:
   (a) incubating the antibody or antigen with the corresponding antibody or antigen being covalently bonded to a solid phase and allowing their reaction to take place in the presence of 0.1 to 3 g/100 g of the aqueous fluid of a surfactant of the formula I $$CH_3-(CH_2)_m-R-(CH_2-CH_2-O)_n-H \quad \text{I}$$

where R is O, NH or $CH=CH-(CH_2)_p-O$, m is 3-26, n is 7-40 and p is 5-15; and
   (b) measuring the reaction between the antibody and antigen, and
   (c) relating said measurement to the amount of antibody or antigen.

2. The method as claimed in claim 1, wherein R is O or $CH=CH-(CH_2)_p-O$ and m is 3-26, n is 7-40 and p is 5-15.

3. The method as claimed in claim 1, wherein R is O or $CH=CH-(CH_2)_p-O$ and m is 15-17, n is 25 and and p is 6-8.

4. The method as claimed in claim 1, wherein R is O or $CH=CH-(CH_2)_p-O$ and m is 6-8, n is 25 and p is 6-8.

5. The method as claimed in claim 1, in which is used a mixture of formula I which contains 20-35% of palmityl alcohol etherified with polyethylene glycol with a degree of polymerization of P=25, 25-30% to stearyl alcohol etherified with polyethylene glycol (P=25) and 30-60% of oleyl alcohol etherified with polyethylene glycol (P=25).

6. The method as claimed in claim 1, in which there are present during the reaction glycine in a concentration of 0.05-0.2 mol/l, NaCl in a concentration of 0.05-0.5 mol/l, polyethylene glycol in a concentration of 4 g/100 g and/or eicosaoxyethylene sorbitan laurate in a concentration of 0.2-1 g/100 g.

7. An agent for carrying out the nephelometric or turbidimetric determination in an aqueous fluid of an antibody or antigen containing
   (a) a buffer substance,
   (b) a compound of the formula I $$CH_3-(CH_2)_m-R-(CH_2-CH_2-O)_n-H$$

wherein R is O, NH, or $CH=CH-(CH_2)_p-O$, m is 3-26, n is 7-40 and p is 5-15; in such an amount that the compound of formula I will be present during antigen-antibody reaction in a concentration of 0.1 to 3 g/100 g of the aqueous fluid, and
   (c) eicosaoxyethylene sorbitan laurate in such a concentration that it will be present during the reaction in a concentration of 0.2 to 1 g/100 g.

* * * * *

UNITED STATES PATENT AND TRADEMARK OFFICE
CERTIFICATE OF CORRECTION

PATENT NO. : 5,232,859
DATED : August 03, 1993
INVENTOR(S) : Wolfgang Kapmeyer et al.

It is certified that error appears in the above-indentified patent and that said Letters Patent is hereby corrected as shown below:

Claim 5, column 8, line 36, change "25-30%" to --15-30%--.

Signed and Sealed this

Twenty-first Day of June, 1994

Attest:

BRUCE LEHMAN

Attesting Officer

Commissioner of Patents and Trademarks